(12) United States Patent
Jones

(10) Patent No.: US 9,261,489 B2
(45) Date of Patent: Feb. 16, 2016

(54) TOOL AND METHOD FOR MANIPULATING A TRANSDUCER ASSEMBLY

(71) Applicant: AIRBUS OPERATIONS LIMITED, Bristol (GB)

(72) Inventor: Terence Jones, Chepstow (GB)

(73) Assignee: AIRBUS OPERATIONS LIMITED, Bristol (GB)

( * ) Notice: Subject to any disclaimer, the term of this patent is extended or adjusted under 35 U.S.C. 154(b) by 349 days.

(21) Appl. No.: 13/736,345

(22) Filed: Jan. 8, 2013

(65) Prior Publication Data

US 2013/0174663 A1 Jul. 11, 2013

(30) Foreign Application Priority Data

Jan. 9, 2012 (GB) .................................. 1200274.7

(51) Int. Cl.
*G01B 15/00* (2006.01)
*G01N 29/22* (2006.01)
*G01N 29/265* (2006.01)

(52) U.S. Cl.
CPC ............ *G01N 29/226* (2013.01); *G01N 29/265* (2013.01); *G01N 2291/2694* (2013.01)

(58) Field of Classification Search
CPC ............... A61N 2007/003; A61N 2007/0056; A61N 1/37282; A61N 1/0502; A61N 1/0553; A61N 1/0556; A61N 1/0558; A61N 1/3601; A61N 1/36025; A61N 1/36082; A61N 1/36103; A61N 1/36139; A61N 1/36014; A61N 2/00; G01N 29/22; G01N 29/225; G01N 29/24; G01N 29/2493; G01N 29/226; G01N 29/265; G01N 2291/2694

USPC .......... 73/61.52, 23.35, 627, 861.18, 864.01; 345/8, 633, 156, 158, 589, 419, 617; 382/128; 702/150, 167, 41
See application file for complete search history.

(56) References Cited

U.S. PATENT DOCUMENTS

| 2,666,862 | A | | 1/1954 | Branson | |
|---|---|---|---|---|---|
| 2,824,979 | A | | 2/1958 | McKee | |
| 3,002,375 | A | | 10/1961 | Moffatt et al. | |
| 3,585,579 | A | * | 6/1971 | Dorr | B06B 1/0622 367/153 |
| 3,732,444 | A | * | 5/1973 | Miller | B06B 1/0655 310/336 |
| 4,027,528 | A | | 6/1977 | Tyree | |
| 4,229,978 | A | * | 10/1980 | Sholl | B06B 1/0215 310/317 |
| 4,453,409 | A | * | 6/1984 | Naumann et al. | 73/639 |
| 4,487,071 | A | * | 12/1984 | Pagano | G01N 29/07 73/612 |
| 4,807,476 | A | * | 2/1989 | Cook et al. | 73/620 |

(Continued)

FOREIGN PATENT DOCUMENTS

EP 1605259 A1 12/2005

OTHER PUBLICATIONS

Search Report corresponding to GB 1200274.7, dated Apr. 20, 2012.
(Continued)

*Primary Examiner* — Laura Martin
*Assistant Examiner* — Samir M Shah
(74) *Attorney, Agent, or Firm* — Hauptman Ham, LLP

(57) ABSTRACT

A tool for manipulating a transducer assembly. The tool had a shaft to space the transducer assembly from a handle end. The tool rotatably mounts the transducer assembly so that the transducer assembly can transmissively coupled to and follow an arcuate scanning path. The tool includes a guide member for following an edge of a component to be tested.

14 Claims, 2 Drawing Sheets

(56) References Cited

U.S. PATENT DOCUMENTS

| | | | | |
|---|---|---|---|---|
| 4,898,034 | A * | 2/1990 | Kupperman | G01N 29/28 73/639 |
| 5,343,750 | A * | 9/1994 | Bashyam | 73/635 |
| 5,404,755 | A * | 4/1995 | Olson | G01N 3/48 73/12.12 |
| 5,419,196 | A * | 5/1995 | Havira | G01N 29/221 73/623 |
| 5,535,628 | A * | 7/1996 | Rutherford | G01N 29/225 73/622 |
| 5,576,492 | A | 11/1996 | Phalin | |
| 6,055,862 | A * | 5/2000 | Martens | G01N 29/2493 73/632 |
| 6,248,072 | B1 * | 6/2001 | Murkin | 600/446 |
| 6,276,209 | B1 * | 8/2001 | Schafer | G01N 29/07 73/597 |
| 6,536,553 | B1 * | 3/2003 | Scanlon | G01N 29/069 181/108 |
| 6,571,636 | B1 * | 6/2003 | McWhorter | G01N 29/2493 73/636 |
| 6,688,178 | B1 * | 2/2004 | Schmidt | G01N 29/2493 73/639 |
| 7,669,477 | B2 * | 3/2010 | Georgeson et al. | 73/623 |
| 2002/0148295 | A1 * | 10/2002 | Shives | G01N 29/22 73/618 |
| 2004/0113625 | A1 * | 6/2004 | Pagano | G01N 29/07 324/334 |
| 2005/0210984 | A1 * | 9/2005 | Sengupta | G01N 29/043 73/635 |
| 2005/0274188 | A1 | 12/2005 | Cabanis et al. | |
| 2007/0119255 | A1 | 5/2007 | Czerw et al. | |
| 2008/0028859 | A1 * | 2/2008 | Figge | G01N 29/225 73/596 |
| 2008/0221454 | A1 * | 9/2008 | Davidsen | G01S 7/5208 600/459 |
| 2008/0232197 | A1 * | 9/2008 | Kojima | G01S 7/521 367/99 |
| 2008/0236286 | A1 * | 10/2008 | Lam | G01N 29/043 73/618 |
| 2012/0060609 | A1 * | 3/2012 | Fukutomi | G01N 29/225 73/592 |

OTHER PUBLICATIONS

European Search Report dated Feb. 28, 2014 in EP Application No. 13150371.6.

* cited by examiner

TOOL AND METHOD FOR MANIPULATING A TRANSDUCER ASSEMBLY

RELATED APPLICATIONS

The present application is based on, and claims priority from, British Application Number 1200274.7, filed Jan. 9, 2012, the disclosure of which is hereby incorporated by reference herein in its entirety.

FIELD OF THE INVENTION

The present invention relates to a tool suitable for manipulating a transducer assembly and to a method of manipulating a transducer assembly.

BACKGROUND OF THE INVENTION

Non-visible areas of materials, such as the interiors of components, welds and composite materials can be analysed using ultrasonic testing. This type of non-destructive testing utilises the reflection of sound waves to detect faults and features which would otherwise be very difficult to detect without destroying the component in the process. Ultrasonic testing is a common technique in the aerospace sector to test the integrity of materials at manufacture and components during service.

If a component within an assembly, such as an aircraft, is to be tested using non-destructive testing it is in some cases necessary to partially disassemble the assembly to access a specific part of the component. The location of the component and the manner in which it is tested may determine the degree of disassembly required. For example, an aircraft forward engine pylon mounting is a well known component that may be analysed for damage using an ultrasonic testing scanner. Such a mounting generally consists of a number of plate-like lugs positioned in a parallel side by side arrangement, each lug having a hole for receiving a common attachment link by which the engine pylon is coupled to the mounting. In testing, an ultrasound transducer is moved across a major face of one or more of the lugs to detect cracks and the like. However, in order to access a major face of the forward engine pylon mounting it is necessary to remove the engine and pylon, which has an adverse effect on servicing time and complexity.

SUMMARY OF THE INVENTION

The present application relates to a tool for manipulating a transducer assembly. The tool had a shaft to space the transducer assembly from a grasping end. The tool rotatably mounts the transducer assembly so that the transducer assembly can transmissively coupled to and follow an arcuate scanning path. The tool includes a guide member for following an edge of a component to be tested.

A first aspect of the invention provides a tool for manipulating a transducer assembly, the transducer assembly having an emission face from which in use an analysis signal is emitted. The tool may comprise an elongate shaft coupled to a transducer receiving portion. The transducer receiving portion may be arranged to be rotatably coupled to the transducer assembly. The tool may include a guide member. The guide member may be arranged in use to project beyond the emission face of the transducer assembly. Thus, a tool according to embodiments of the present invention may be used to manipulate a transducer assembly along an arcuate scanning surface which is difficult to access by hand. The transducer assembly may pivot about the tool to remain transmissively coupled to the scanning surface as the tool is moved. The guide member can be used to follow an edge, which may increase scan accuracy and repeatability.

The guide member may be arranged to project beyond the emission face when the transducer assembly is at a plurality of different angular positions. This may improve the utility of the tool as different arcs and gradients may be scanned.

The transducer receiving portion may comprise first and second arms arranged to be rotatably coupled to respective opposite sides of the transducer assembly.

The arms may be generally planar and positioned so as to be orthogonal to the rotational axis of the transducer. This may provide a laterally compact tool.

The tool may include a shoe arranged to be transmissively coupled to the transducer so as to form the transducer assembly. The shoe may be arranged to be rotatably coupled to the transducer receiving portion of the tool such that the shoe may pivot about the rotational axis.

The emission face may have a concave outer profile.

The tool may be in combination with the transducer assembly.

The transducer assembly may be an ultrasound transducer assembly. The analysis signal may be ultrasound.

The tool may be arranged to be manipulated by hand; for example, a distal portion of the shaft may be provided with, or may define, a handle.

A further aspect of the invention provides use of the tool according to the first aspect as a manipulator for a transducer assembly during non-destructive testing of a component.

A further aspect of the invention provides a method of manipulating a transducer assembly. The method may comprise providing a tool according to the first aspect. The method may comprise positioning the tool such that the guide member is adjacent or in contact with a guide surface of the component and the transducer assembly is transmissively coupled to a scanning surface of the component. The method may comprise moving the transducer assembly along the scanning surface such that the guide member remains adjacent or in contact with the guide surface.

The method may include moving the transducer of the transducer assembly to a different position within the shoe of the transducer assembly.

The method may include rotating the tool about its longitudinal axis L by 180° and positioning the tool such that the guide member is adjacent or in contact with a second guide surface of the component and the transducer assembly is transmissively coupled to a scanning surface of the component.

The scanning surface may be arcuate.

The scanning surface may be positioned within a narrow recess.

The transducer assembly may be an ultrasound transducer assembly.

BRIEF DESCRIPTION OF THE DRAWINGS

Embodiments of the invention will now be described with reference to the accompanying drawings, in which.

DETAILED DESCRIPTION OF EMBODIMENT(S)

Figure 1:
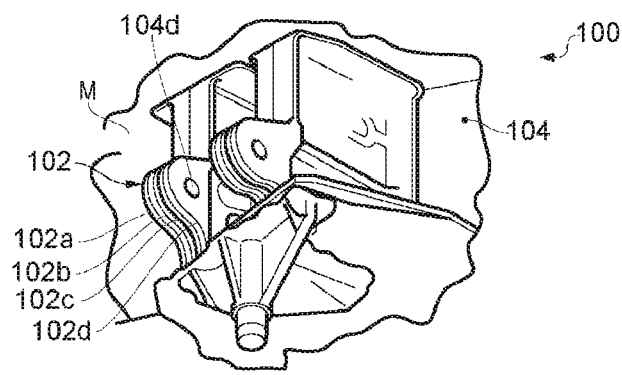
FIG. 1 is a diagram showing a known aircraft forward engine pylon mounting.
Figure 2:
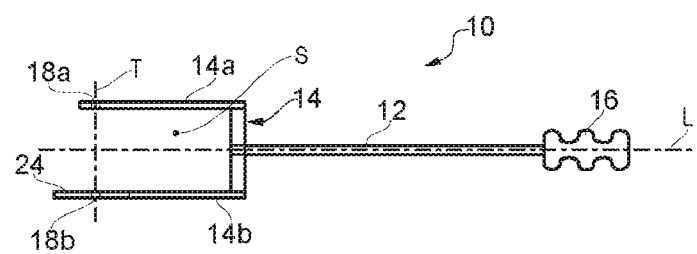
FIG. 2 is a diagram showing a plan view of a tool according to an embodiment of the present invention.
Figure 3:
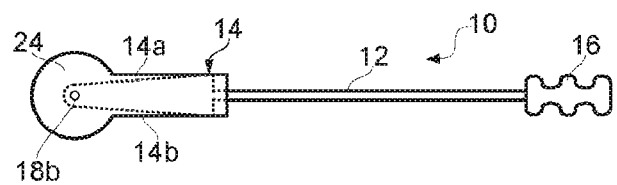
FIG. 3 is a diagram showing a side view of the tool of FIG. 2.
Figure 4:
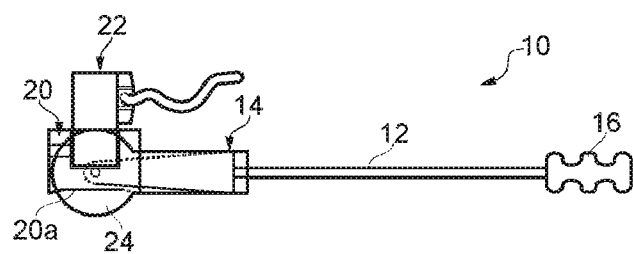
FIG. 4 is a diagram showing a side view of the tool of FIG. 2 with a transducer assembly mounted thereto.

FIG. 1 shows part of an aircraft 100 including a known forward engine pylon mounting/fitting which will be referred to as a "pylon mounting" 102. The pylon mounting 102 is attached to the front spar 104 of the aircraft 100 and consists of four plate-like lugs 102a-102d positioned in a parallel, side by side arrangement. Each lug 102a-102d has a lateral hole 104d for receiving a common attachment link (not shown) by which the engine pylon (not shown) may be coupled to the mounting 102.

Over time, cracks or other damage may occur within the pylon mounting 102 and it is desirable to check for damage by non-destructive testing; for example, the condition of the mounting lugs 102a-102d can be analysed using ultrasonic testing.

Figure 6:
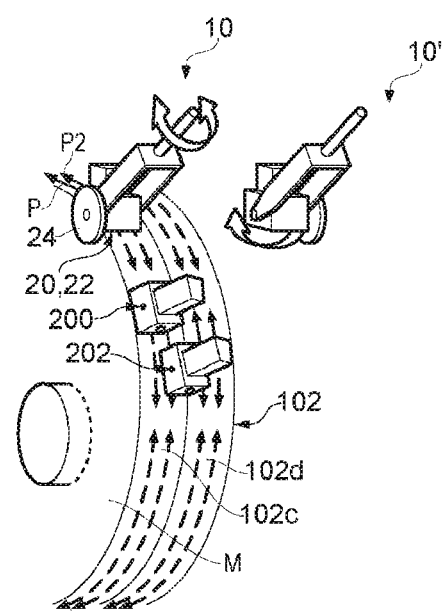
FIG. 6 is a diagram illustrating a method of using the tool.

It is known to move an ultrasound transducer across a major face M of the mounting 102. However, this requires removal of the engine pylon. The present inventor has discovered that each lug 102a-102d may instead be scanned along an edge surface (see FIG. 6) to check for damage using ultrasonic testing. One problem however is that the upper and/or lower regions of the edge surfaces are difficult to access due to adjacent components. This is particularly problematic on the A340, A500 and A600 aircraft produced by Airbus, although the same is true for many aircraft. Similar problems exist when trying to scan a surface which is disposed within a narrow recess i.e. a recess which is sized and/or configured such that it is difficult for a user to hold a transducer in their hand and move it across the scanning surface. Such a recess may be formed by components which are adjacent the scanning surface.

Referring to FIGS. 2 to 5, a tool 10 according to an embodiment of the present invention is shown. The tool 10 is arranged to enable a user to move an ultrasound or other non-destructive testing transducer along a surface which is disposed within a narrow recess. The effective length of the tool 10, i.e. the distance from the transducer to the grasping end, may be any suitable length; for example, at least 25 mm, 50 mm, 75 mm, 100 mm, 125 mm or 150 mm and/or less than 1 m, 750 mm, 500 mm, 250 mm, 150 mm or 100 mm.

The tool 10 includes an elongate shaft 12 having a first end attached to a transducer receiving portion 14 and a second end which may optionally be provided with a handle 16. The shaft 12 may be between 10 mm and 150 mm in length and preferably between 25 mm and 75 mm. The shaft may be formed of any suitable material, such as spring steel and may have any suitable shape and configuration.

In the illustrated embodiment the transducer 22 is transmissively coupled to a shoe 20 such that ultrasound may be transmitted to and received from a target feature via the shoe. The transducer 22, with or without a shoe 20, will for simplicity be referred to herein as a "transducer assembly". The tool 10 may be used with any suitable transducer assembly 20, 22.

In the illustrated embodiment the transducer 20 is an 8 mm×8 mm 16 element probe such as one marketed my Olympus NDT Limited under the part number U8330589.

Figure 5:
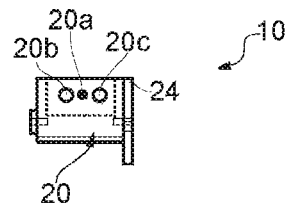
FIG. 5 is a diagram showing a front view of the tool of FIG. 4.

The shoe is formed from a plastics material having, in this embodiment, a sound velocity of 2330 meters per second and, as shown in FIG. 5, includes a recess 20a which is wider than the transducer 22 and thus can receive the transducer 22 at various lateral positions. Locking elements 20b, 20c, such as screws which may be advanced into the recess 20a, are provided to lock the position of the transducer 22 within the shoe 20.

The transducer receiving portion 14 is arranged to be rotationally coupled to an ultrasound transducer 22. In the illustrated embodiment the transducer receiving portion 14 comprises a pair of elongate arms 14a, 14b which extend generally parallel to the longitudinal axis L of the shaft 12. The arms 14a, 14b may be formed of any suitable material, such as spring steel. The arms 14a, 14b are situated on opposite sides of the longitudinal axis L of the shaft 12 so as to define a receiving space S between them. The receiving space S is sized to receive the transducer assembly 20, 22 and in the illustrated embodiment 19 mm wide, although it may be of any suitable size.

A rotational coupling element 18a, 18b is provided towards a free end of each arm 14a, 14b. The coupling elements 18a, 18b define an axis T about which the transducer assembly 20, 22 may rotate. In the illustrated embodiment the rotational coupling elements are a pair of holes 18a, 18b, each arranged to receive a projection extending from a shoe 20 in which the ultrasound transducer 22 is situated. However, in other embodiments the coupling elements 18a, 18b may couple to the transducer assembly 20, 22 in any suitable manner; for example the coupling elements 18a, 18b may comprise projections and/or may alternatively be arranged to attach directly to the transducer 22.

In the illustrated embodiment the arms 14a, 14b are generally rectangular, each having two generally flat and parallel major faces. The general plane defined by each major face is generally orthogonal to the axis T about which the transducer may rotate. The combination of thin, flat arms 14a, 14b configured as such results in a laterally compact tool 10 which is useful when scanning surfaces which are difficult to access; for example, a surface within a narrow recess.

The transducer assembly 20, 22 includes a surface from which ultrasound is emitted in use; this will be referred to as the "emission surface 20a". The emission surface 20a may be profiled to conform to the surface it is arranged to scan. Thus, the emission surface 20a of a transducer assembly 20, 22 arranged to scan the arcuate regions of an A340, A500 or A600 pylon mounting 102 may have a laterally concave profile with a radius of curvature of at least 76.2 mm. By "arcuate" it is meant that the pitch or gradient of the scanning path varies along its length; for example, the arc may be convex or concave relative to the user, or a mixture of these. The invention may be used with any such structure; for example, aileron, rudder or elevator attachment lugs.

The tool 10 also includes a guide member 24 which projects beyond the "emission surface 20a". The guide member 24 is positionally fixed with respect to the transducer assembly 20, 22 in the direction of axis T and thus may be used to guide the transducer assembly 20, 22 along a path which follows an edge or groove. Preferably the guide member 24 is arranged such that in use it does not overlap the emission surface 20a i.e. the guide member 24 is adjacent or spaced from the emission surface 20a along axis T, meaning that the entire emission surface 20a may be coupled to a scanning surface while the guide member 24 is adjacent or in contact with a guide surface.

In the illustrated embodiment the guide member 24 is a generally disc shaped continuation of the arm 14b, positioned such that its centre is generally coaxial with the axis T about which the transducer assembly 20, 22 may rotate. The guide member 24 extends radially such that its circumferential edge projects beyond the emission surface 20a. Thus, the guide member 24 functions throughout a 270° arc of rotation of the transducer assembly 20, 22, which may be advantageous when scanning an arcuate surface. Moreover, the tool 10 be rotated about its longitudinal axis L by 180° to change from guiding the transducer assembly 20, 22 along, say, a left hand edge to a right hand edge, thereby increasing the utility of the tool 10.

In other embodiments the guide member 24 may take any suitable form in which it projects beyond the emission surface 20a when the transducer assembly 20, 22 is at one or more rotational positions; for example, the guide member 24 may be generally "T" shaped and side on such that side projections of the "T" extend in a generally orthogonal manner with respect to both the longitudinal axis L of the shaft 12 and the rotational axis T of the transducer assembly 20, 22. In some embodiments the distance from the axis T to the distal edge of the guide member 24 may be at least 25%, 40% or 50% of the width of the receiving space S, the width being parallel to the axis T.

FIG. 5 illustrates a method of scanning a pylon mounting 102 using a tool 10 according to an embodiment of the invention. As shown, the tool 10 is positioned such that the guide member 24 is against a guide surface of a first lug 102c of the pylon mounting 102 and, with the transducer 22 positioned and locked within the shoe 20 such that it is at its closest position to the guide member 24, the transducer assembly 20, 22 is moved along a scanning path P at one side of the edge of the lug 102c.

The transducer 22 may be positioned and locked within the shoe 20 such that it is at its furthest position from the guide member 24 and moved along a scanning path P2 at the opposite side of the edge of the lug 102c.

As shown, the tool may be rotated about its longitudinal axis L by 180°, shown as 10', such that the edge of lug 102d may be scanned in a similar manner.

Thus, a tool according to embodiments of the present invention may be used to manipulate a transducer assembly along an arcuate scanning surface which is difficult to access by hand. The transducer assembly may pivot about the tool to remain transmissively coupled to the scanning surface as the tool is moved. The guide member can be used to follow an edge to increase the accuracy and repeatability of the scanning path, which may otherwise deteriorate with distance from the user.

Although the invention has been described above with reference to one or more preferred embodiments, it will be appreciated that various changes or modifications may be made without departing from the scope of the invention as defined in the appended claims.

The invention claimed is:

1. An apparatus, comprising a transducer assembly and a tool for manipulating the transducer assembly, the transducer assembly having an emission face from which, in use, an analysis signal is emitted, the tool comprising an elongate shaft coupled to a transducer receiving portion, the transducer receiving portion being rotatably coupled to the transducer assembly, and a guide member arranged to project beyond the emission face of the transducer assembly, wherein the emission face of the transducer assembly has a concave outer profile, which conforms to an arcuate scanning surface of an aircraft component.

2. An apparatus according to claim 1, wherein the guide member is arranged to project beyond the emission face when the transducer assembly is at a plurality of different angular positions.

3. An apparatus according to claim 1, wherein the transducer receiving portion comprises first and second arms arranged to be rotatably coupled to respective opposite sides of the transducer assembly.

4. An apparatus according to claim 3, wherein the transducer assembly comprises a transducer, and wherein the arms are generally planar and positioned so as to be orthogonal to the rotational axis of the transducer.

5. An apparatus according to claim 1 including a shoe arranged to be transmissively coupled to a transducer so as to form the transducer assembly, the shoe being arranged to be rotatably coupled to the transducer receiving portion of the tool such that the shoe may pivot about the rotational axis of the transducer.

6. An apparatus according to claim 1, wherein the transducer assembly is an ultrasound transducer assembly and the analysis signal is an ultrasound signal.

7. An apparatus according to claim 1, wherein the tool comprises a handle.

8. A method of manipulating a transducer assembly for inspecting a component of an aircraft assembly, the transducer assembly having an emission face from which in use, an analysis signal is emitted, the method comprising:
providing a tool for manipulating the transducer assembly, the tool comprising an elongate shaft coupled to a transducer receiving portion, the transducer receiving portion being arranged to be rotatably coupled to the transducer assembly, and a guide member, the guide member being arranged in use, to project beyond the emission face of the transducer assembly;
positioning the tool such that the guide member is adjacent or in contact with a guide surface of the component of the aircraft assembly and the transducer assembly is transmissively coupled to an arcuate scanning surface of the component of the aircraft assembly; and
moving the transducer assembly along the scanning surface such that the guide member remains adjacent or in contact with the guide surface,
wherein the emission face of the tranducer assembly has a concave outer profice conforming to the arcuate scanning surface of the component of the aircraft assembly.

9. A method according to claim 8, wherein the transducer assembly comprises a transducer and a shoe, and wherein the method further includes moving the transducer of the transducer assembly to a different position within the shoe of the transducer assembly.

10. A method according to claim 8, including rotating the tool about its longitudinal axis by 180° and positioning the tool such that the guide member is adjacent or in contact with a second guide surface of the component and the transducer assembly is transmissively coupled to the scanning surface of the component of the aircraft assembly.

11. A method according to claim 8, wherein the scanning surface is positioned within a substantially narrow recess.

12. A method according to claim 8, wherein the transducer assembly is an ultrasound transducer assembly.

13. A method according to claim 8, wherein the scanning surface of the component comprises a major face of the component, and the guide surface of the component comprises an edge surface of the component.

14. A method according to claim 13, wherein the guide surface of the component is at least partially obscured by another component of the aircraft assembly.

* * * * *